United States Patent [19]

Asaoka

[11] Plant 4,660

[45] Mar. 3, 1981

[54] ROSE PLANT - SUPRENSE

[75] Inventor: Keisuke Asaoka, Nishio, Japan

[73] Assignee: Jackson & Perkins Co., Medford, Oreg.

[21] Appl. No.: 104,566

[22] Filed: Dec. 17, 1979

[51] Int. Cl.[3] ..... A01H 5/00

[52] U.S. Cl. ..... Plt./23

[58] Field of Search ..... Plt./23

*Primary Examiner*—Robert E. Bagwill

*Attorney, Agent, or Firm*—Klarquist, Sparkman, Campbell, Leigh, Hall & Whinston

[57] ABSTRACT

This novel rose variety is a mutation of Faberge, U.S. Plant Pat. No. 2,886, and differs therefrom in its bud color which is of a yellow color and blossoms which are of a greenish white to white color.

1 Drawing Figure

DETAILED DESCRIPTION OF INVENTION

The present invention relates to a new and distinct variety of rose plant of the floribunda class, which was discovered by me as a cultivated sport of the hybrid tea rose Faberge (U.S. Plant Pat. No. 2,886), on a plant grown in Japan.

On a Faberge rose bush, I discovered that the blossoms on one of the branches were distinctly different from the normal Faberge in that the buds were of a yellow color close to RHS Colour Chart 4D while the open flowers were of a greenish white close to RHS 157C to white, the petal tips being of a very light pink. Propagation of the budding eyes on this one stem in Japan proved that this sport came through on successive propagations.

This new cultivar is substantially identical in all respects to its parent, except for the difference in bud and blossom color noted above.

The attached drawing shows the new cultivar in color as nearly true as it is reasonably possible to make the same in a color illustration of this character.

Being substantially identical to the parent variety, except for the aforementioned distinctions, reference is made to U.S. Plant Pat. No. 2,886 for a further description of this variety.

I claim:

1. A new and distinct variety of rose plant of the floribunda class, substantially as herein shown and described, characterized particularly as to novelty by the yellow hue of the bud and the greenish white to white bloom on the plant otherwise identical to the variety Faberge.

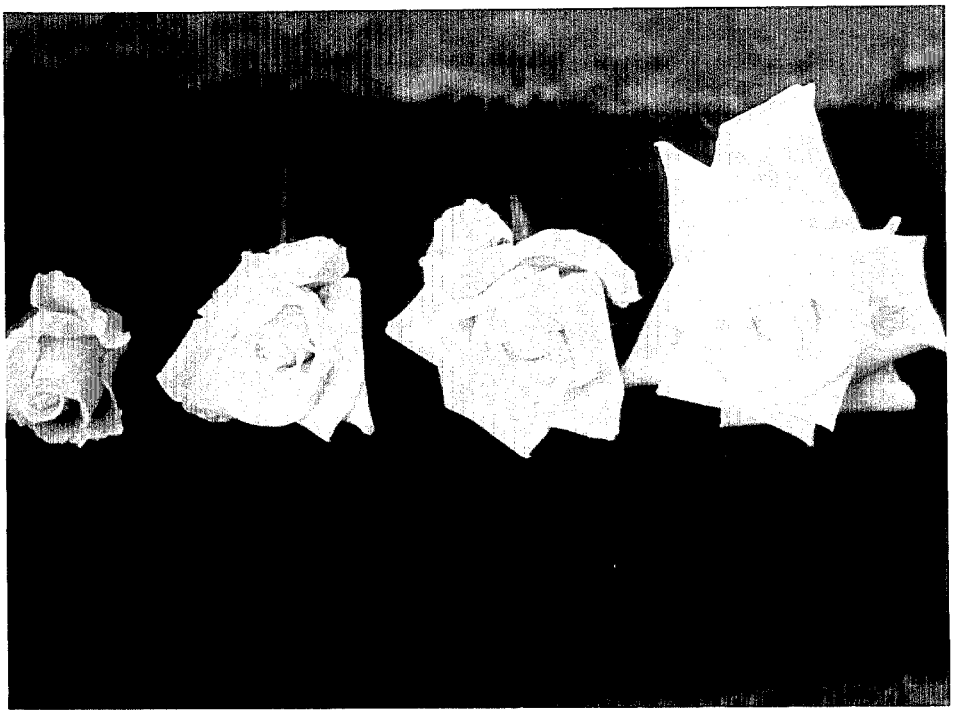

* * * * *